US006800612B2

(12) United States Patent
Repolles Moliner et al.

(10) Patent No.: US 6,800,612 B2
(45) Date of Patent: Oct. 5, 2004

(54) S-NITROSOTHIOLS AS AGENTS FOR THE TREATMENT OF CIRCULATORY DYSFUNCTIONS

(75) Inventors: José Repolles Moliner, Barcelona (ES); Eduardo Salas Perez-Rasilla, Barcelona (ES); Francisco Pubill Coy, Barcelona (ES); Juan-Antonio Cerda Riudavets, Sabadell (ES); Cristina Negrie Rofes, Leiden (NL); Lydia Cabeza Llorente, Barcelona (ES); Alicia Ferrer Siso, Barcelona (ES); Nuria Trias Adroher, Barcelona (ES); Marcel.li Carbo Banus, Barcelona (ES); Jesús Murat Moreno, Barcelona (ES); Pedro Michelena Llagundo, Barcelona (ES)

(73) Assignee: Lacer, S.A., Barcelona (ES)

( * ) Notice: Subject to any disclaimer, the term of this patent is extended or adjusted under 35 U.S.C. 154(b) by 0 days.

(21) Appl. No.: 09/912,164

(22) Filed: Jul. 24, 2001

(65) Prior Publication Data

US 2002/0058629 A1 May 16, 2002

Related U.S. Application Data

(63) Continuation of application No. PCT/ES00/00019, filed on Jan. 19, 2000.

(51) Int. Cl.$^7$ .................................................. C07K 5/06

(52) U.S. Cl. ........................... 514/19; 514/18; 562/553; 562/558

(58) Field of Search ...................... 514/19, 18; 562/553, 562/558; 530/331

(56) References Cited

U.S. PATENT DOCUMENTS

| | | | | |
|---|---|---|---|---|
| 4,137,236 | A | 1/1979 | Rodriguez et al. | ....... 260/306.7 |
| 4,271,172 | A | 6/1981 | Rodriguez et al. | .......... 424/267 |
| 5,187,305 | A | 2/1993 | Thompson et al. | ......... 560/145 |
| 5,968,911 | A | 10/1999 | Lawson et al. | ................ 519/46 |
| 2002/0037839 | A1 | 3/2002 | Stamler et al. | ................ 514/6 |

FOREIGN PATENT DOCUMENTS

| | | |
|---|---|---|
| EP | 0330094 | 8/1989 |
| EP | 0 412 699 A2 | 2/1991 |
| EP | 0 412 699 A3 | 2/1991 |
| EP | 0 412 699 B1 | 2/1991 |
| RU | 2106357 | 3/1994 |
| RU | 2046798 | 10/1995 |
| RU | 96121403 | 2/1999 |
| WO | WO 89/12627 | 12/1989 |
| WO | WO 93/09806 | 5/1993 |
| WO | WO 95/07691 | 3/1995 |
| WO | WO 95/12394 | 5/1995 |
| WO | WO 96/16645 | 6/1996 |
| WO | WO 98/42753 | 10/1998 |

OTHER PUBLICATIONS

Abstract of Russian Patent No. 2119332, published Sep. 27, 1998, which is the same as Russian Patent No. 95108432 A1.
Abstract of Russian Patent No. 2142469.
Abstract of Russian Patent No. 2142939, published Dec. 20, 1999.
Giustarini, D. et al., "Nitric oxide and S–nitrosothols in human blood", *Clinica Chimica Acta*, 330(1–2): 85–98 (2003).
Radomski, R. et al. "Systemic effects of S–nitroso–glu-athione in the human following intravenous infusion", *British Journal of Pharmacology*, 40(1): 101–102 (1995).
de Belder, A. et al. "Effects of S–nitroso–glutathione in the human forearm circulations: evidence for selective inhibition of platelet activation", *Cardiovascular Research*, 28: 691–694 (1994).
Stamler, J. et al. "Endothelium–Derived Relaxing Factor Modulates the Atherothrombogenic Effects of Homocysteine", *Journal of Cardiovascular Pharmacology*, 20(12): 202–204 (1992).

(List continued on next page.)

*Primary Examiner*—Christopher S. F. Low
*Assistant Examiner*—David Lukton
(74) *Attorney, Agent, or Firm*—Scully, Scott, Murphy & Presser

(57) ABSTRACT

The present invention is directed to a S-nitrosothiol derivative of penicillamine or glutathione, of formula I:

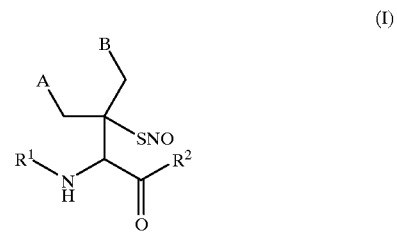

(I)

or its pharmaceutically acceptable salt thereof, in which: A and B are independently phenyl groups or together form the group —$CH_2$—Q—$CH_2$—constituting a six membered ring in which Q represents oxygen, sulfur, or a group N—$R^3$, in which $R^3$ is hydrogen or a $C_1$–$C_4$ alkyl group; $R^1$ is an acyl group, which may be an aliphatic $C_1$–$C_5$ acyl group or an acyl group of glutamic acid bonded via its gamma carboxyl group; $R^2$ is a hydroxyl group or a glycine group bonded via a peptide bond; with the proviso that if $R^1$ is an aliphatic acyl group, then $R^2$ is a hydroxyl group, and if $R^1$ is a glutamic acid, then $R^2$ is a glycine group. The compounds have vasodilating activity and inhibit the aggregation of the platelets which make them useful for the treatment of dysfunctions of the circulating system, especially at the cardiovascular level. The present invention is also directed to pharmaceutical compositions containing same.

23 Claims, No Drawings

OTHER PUBLICATIONS

Megson, I. et al. "Inhibition of human platelet aggregation by a novel S–nitrosothiol is abolished by haemoglobin and red blood cells in vitro: implication s for anti–thrombotic therapy", *British Journal of Pharamcology*, 131: 1391–1398 (2000).

Inbal, A. et al. "Unique Antiplatelet Effects of a Novel S–Nitrosoderivative of a Recombinant Fragment of von Willebrand Factor, AR545C: In Vitro and Ex Vivo Inhibition of Platelet Function", *Blood*, 94(5): 1693–1700 (1999).

Radomski, et al., "S–nitroso–glutathione inhibits platelet activation in vitro and in vivo," Br. J. Pharmacol, (1992), 107, pp. 745–749.

Golino, et al., "Endothelium–Derived Relaxing Factor Modulates Platelet Aggregation in an In Vivo Model of Recurrent Platelet Activation," Circulation Research, vol. 71, No. 6, (1992), pp. 1447–1456.

Lawson, et al., "Pharmacology of a Human Dopamine D4 Receptor Expressed in HEK293 Cells," Meth Find Exp Clin Pharmacol, (1994), 16(5), pp. 303–307.

Kaiser, et al., "Color Test for Detection of Free Terminal Amino Groups in the Solid–Phase Synthesis of Peptides," Anal, Biochem., 34, (1970), pp. 595–598.

Furchgott, "Bioassays with Isolated Vascular Tissue for Endothelium–derived Relaxing Factor, Nitric Oxide and Nitric Oxide Donors," Feelisch & Stamler Eds., John Wiley & Sons, Chichester, England, (1996), pp. 567–581.

Trongvanicham, et al., "Effects of Chronic Oral Administration of Isosorbide Dinitrate on In Vitro Contractility of Rat Arterial Smooth Muscle," Jpn. J. Pharmacol, (1996), 71, pp. 167–173.

Salas, et al., "Endotheliem–independent relaxation by 17–a–estradiol of pig coronary arteries," Eur. J. Pharmacol., (1994), 258, pp. 47–55.

Loscalzo, et al., "Platelet Bioassays of Nitric Oxide and Related Congeners," Feelisch & Stamler Eds., John Wiley & Sons, Chichester, England,, (1996), pp. 583–591.

Radomski, et al., "Comparative pharmacology of endothelium–derived relaxing factor, nitric oxide and prostacyclin in platelets," Br. J. Pharmacol, (1987), 92, pp. 181–187.

Moro, et al., "Comparative pharmacology of analogues of S–nitroso–N–acetyl–DL–penicillamine of human platelets," Br. J. Pharmacol, (1994), 112, pp. 1071–1076.

Moro, et al., "cGMP mediates the vascular and platelet actions of nitric oxide: Confirmation using an inhibitor of the soluble guanylyl cyclase," Proc. Nat. Acad. Sci. USA, (1996), 93, pp. 1480–1485.

Butler, et al., "Synthesis Decomposition and Vasodilator Action of Some New S–Nitrosated Dipeptides," Nitric Oxide: Biology and Chemistry, vol. 2, No. 3, pp. 193–202, (1998).

Humphrey, et al., "Preparation of Some Novel S–Nitroso Compounds as Potential Slow–release Agents of Nitric Oxide in vivo," J. Chem. Co., Perkin Trans. I, (1994), pp. 797–805.

Mathews, et al., "Biological Activity of S–Nitrosothiols: The Role of Nitric Oxide," J. Pharmacol. and Exp. Therapeutics, 267(8), (1993), pp. 1529–1537.

Dicks, et al., "Identification of Cu+ as the effective reagent in nitric oxide formation from S–nitrosothiols (RSNO)," J. Chem. Soc., PerkinTrans. 2, (1996), pp. 481–487.

S-NITROSOTHIOLS AS AGENTS FOR THE TREATMENT OF CIRCULATORY DYSFUNCTIONS

This is a continuation of Application No. PCT/ES00/00019, filed Jan. 19, 2000.

FIELD OF THE INVENTION

The present invention relates to novel S-nitrosothiols derivatives of penicillamine or glutathione having vasodilating effect and which inhibit the aggregation of the platelets and which therefore are useful for the preparation of medicaments for treatment of dysfunctions of the circulatory system, specially at cardiovascular level.

BACKGROUND OF THE INVENTION

It is well known that compounds capable of releasing nitrogen oxide (NO) into the organism exhibit in many cases some type of activity of the vascular system, for example vasodilating activity or inhibition of the aggregation of the platelets, which make them potentially useful for the treatment of different disorders related to dysfunctions of the circulatory system.

Further, it is described too that specific derivatives which contain a S-nitrosothiol group have, from a medical point of view, advantageous characteristic due to that they are capable of releasing NO in the organism.

Radomski et al., Br. *J. Pharmacol.* (1992) 107, 745–749, describes that the S-nitrosoglutathione (GSNO) compound are capable of inhibiting the activity of the platelets.

Golino et al, *Circulation Research*, 71, No 6 (1992), describes that S-nitrosocysteine is capable of inhibiting the activity of the platelets, due to an effect of anti-thrombosis.

Smith et al., *Met. Find. Exp. Cline. Pharmacy.* (1994), 16, 5, describes that the GSNO produces a strong relaxing effect of the arterioles.

WO95/12394 describes the use of S-nitroso adducts of peptides, among others the S-nitroso-N-acetylpenicillamine (SNAP), as protecting agents against vascular inflammation of traumatic origin.

WO95/07691 describes the use of different S-nitrosothiols, in particular the GSNO, in the treatment and prevention of the action of the platelets and the formation of thrombosis at the damaged vascular surface.

WO93/09806 describes S-nitrosated proteins or amino acid residues, capable of releasing NO, which have a relaxing effect on the musculature and an inhibitory effect on platelet aggregation.

EP-B1-412699 describes S-nitrosothiols which correspond to following general formula:

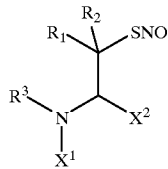

and its use as therapeutic agents against cardiovascular diseases, in particular as anti-hypertension (increased blood pressure) and as agents for the treatment of angina pectoris. The number of possible compounds within said formula is enormous and the description only explicitly describes several tens of such products. Further, there is only disclosed data concerning their general vasodilating effect, and nothing is mentioned in relation to the activity on the platelets.

The S-nitrosothiols described by the documents mentioned above do not by itself solve all the complicated problems within the treatment of vascular disorders, specially at cardiovascular level. It is therefore necessary to develop new compounds which are more potent and effective.

SUMMARY OF THE INVENTION

An object of the present invention relates to novel S-nitrosothiols derivatives of penicillamine or glutathione, which both have a potent vasodilating effect and a high inhibitory effect on the aggregation of the platelets.

Further, an object of the present invention relates to the use of the novel compounds for the manufacture of medicaments for the treatment of disorders related to dysfunctions of the circulatory system, specially at cardiovascular level.

DETAILED DESCRIPTION OF THE INVENTION

The compounds of the invention are S-nitrosothiols derivatives of penicillamine or glutathione, and its pharmaceutically acceptable salts, which correspond to following general formula(I)

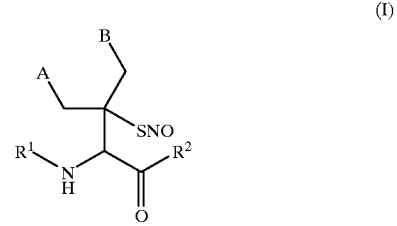

in which:

A and B are phenyl groups or together form the rest —$CH_2$—Q—$CH_2$— constituting a ring of six units in which Q represents an atom of oxygen, of sulfur, or a group N-$R^3$, in which $R^3$ is hydrogen or an alkyl group $C_1$–$C_4$;

$R^1$ is an acyl rest, which may be an aliphatic acyl group $C_1$–$C_5$ or a rest of glutamic acid bound via its non amino acid carboxyl;

$R^2$ is a hydroxyl group or a glycine rest bound via a peptide bond;

with the proviso that if $R^1$ is an aliphatic acyl rest then $R^2$ is a hydroxyl group, and if $R^1$ is a rest of glutamic acid then $R^2$ is a glycine rest Consequently, the compounds of the invention correspond to following general formulas (II) or (III)

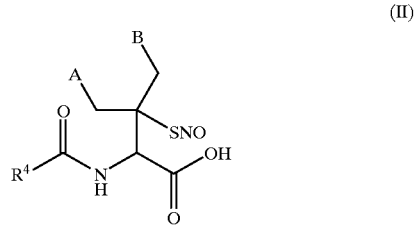

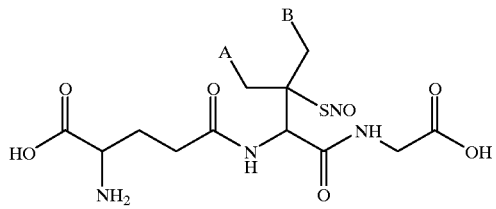

(III)

in which A and B have the meanings mentioned above and R⁴ is an alkyl group $C_1$–$C_4$, or a pharmaceutical acceptable salt of this.

Preferred examples of compounds within the object of the invention are following: N-acetyl-2-amino-2-[4-(4-S-nitrosomercaptotetrahydro-pyran-pyran)] acetic acid (1).

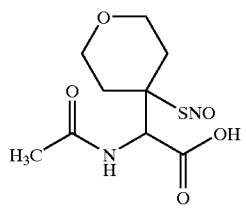

N-acetyl-2-amino-2-[4-(4-S-nitrosomercapto-1-methylpiperidin)]acetic acid (2).

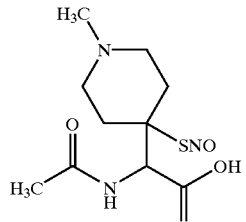

N-acetyl-2-amino-3-benzyl-3-S-nitrosomercapto-4-phenyl-butanoic acid (3).

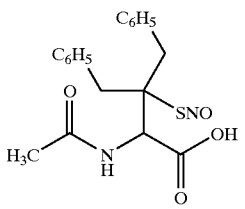

N[N-γ-L-glutamyl-2-amino-2-(4-(4-S-nitrosomercapto)tetrahy-dropyran))acetyl]-glycine(4).

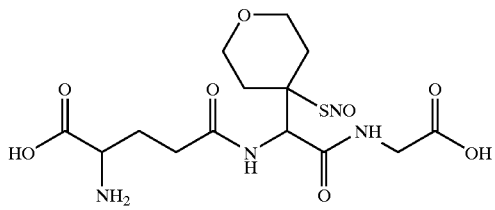

N[N-γ-L-glutamyl-2-amino-2-(4-(4-S-nitrosomercapto-1-methyl-piperidin))acetyl]-glycine (5).

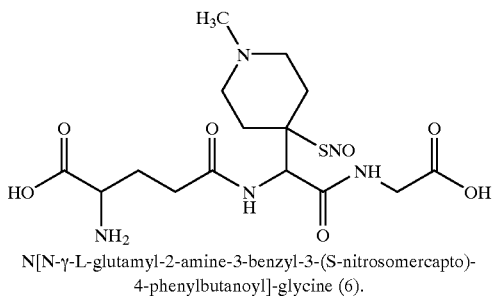

N[N-γ-L-glutamyl-2-amine-3-benzyl-3-(S-nitrosomercapto)-4-phenylbutanoyl]-glycine (6).

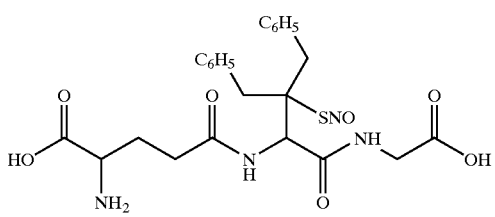

For the skilled person it is obvious that the compounds of the invention comprise chiral centers and this permits to distinguish between the possible isomers and/or the mixtures of these. It should be understood that both the mixtures of isomers and the pure isomers are within the object of the invention. The latter may be obtained from the mixtures of isomers through conventional techniques well known to the expert or through asymmetrically synthesis also well known to him.

The compounds of the invention may be obtained in different manners and the specific manner will generally depends of its basic structure.

For example, the compounds of the general formula (II) may be obtained according to the sequence of steps illustrated in the following scheme.

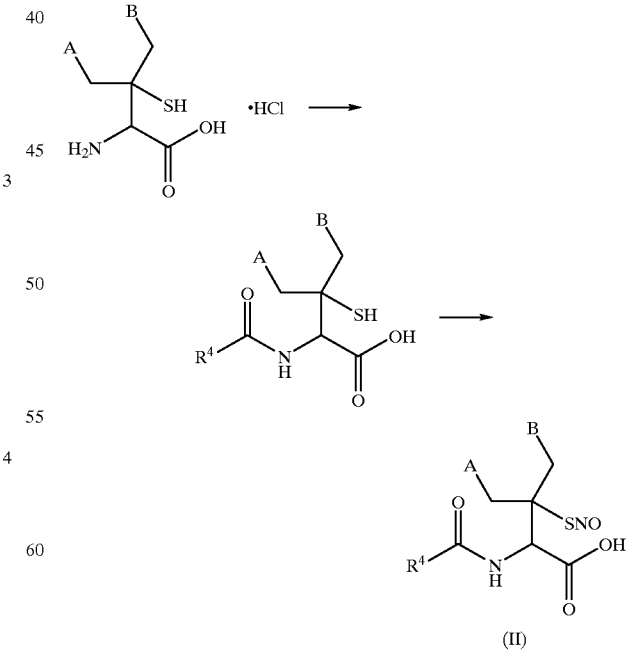

I.e., starting from the chlorhydrates of the amino acids, which may be obtained according to known methods (see e.g. DE-A-3023830 and DE-A-2801849), followed by an acylation of the amino acid nitrogen group through conventional techniques, for example by an acid chloride, and in an final step is then introduced a nitroso group at the mercaptanic sulphur, also by use of conventional techniques.

In relation to the compounds of the general formula (III), they may be obtained according to the sequence of steps illustrated in the following scheme.

activity which is, at least, comparable to that of the GSNO, and in some cases highly superior. Further, they have an inhibitory effect on the aggregation of the platelets which also results to be similar or superior as compared to the GSNO, in some cases considerably superior.

This results in that the compounds of the invention may be used in a very efficient manner for the manufacture of a medicament with vasodilating and anti-thrombotic effect for

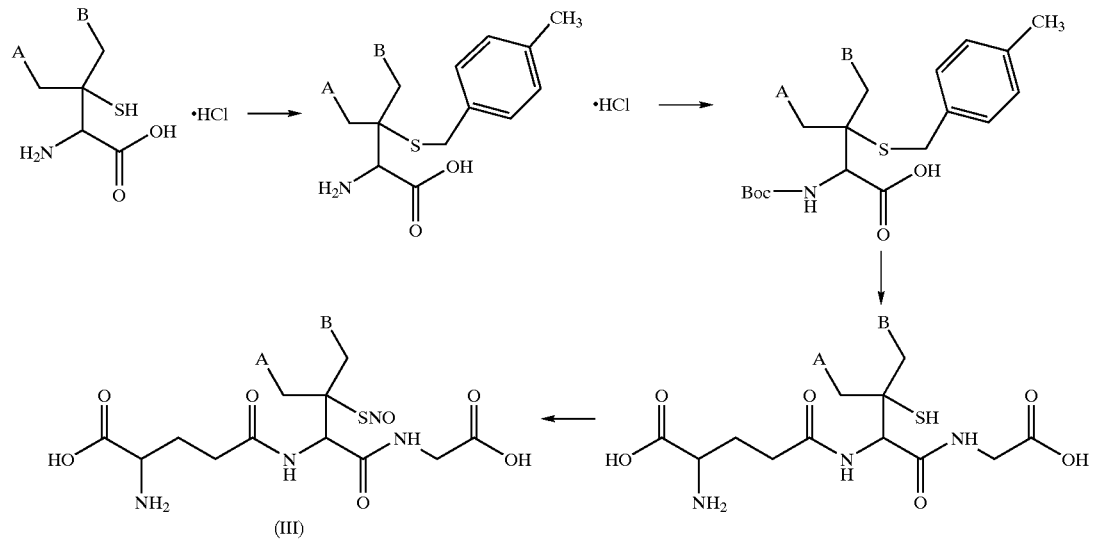

I.e., starting from the same chlorhydrates of the amino acids as in the case above, followed by a protection of the mercapto group through the formation of a thioether of p-methylbenzyl. This is followed by a protection of the amino acid nitrogen through the known technique of Boc and thereafter is formed the tripeptide with the rests Glutamic acid and Glycine (amino acid C-terminal) in solid phase through known techniques (see e.g. Barany, G. et al., *The Peptides*, 2,1, Gross, E. Meienhofer, Eds.Academic Press, NY (1980); Stewart, J. M. et al., *Solid Phase Peptide Synthesis*, Freeman, San Francisco, Calif. (1969); Bodanszky, M. Et al., *Peptide Synthesis*, $2^{nd}$ ed., Wiley, N.Y. (1976)).

The formation of the tripeptide comprises following steps:
   a) Anchoring the amino acid C-terminal Glycine (Gly), in form of a tert-butoxycarbonyl (Boc) derivative, at a resin of p-methylbenzylhydrylamine/polystyrene.
   b) Removing the Boc group with trifluoroacetic acid and neutralization.
   c) Incorporating the intermediate protected modified amino acid.
   d) Evaluating the coupling reaction via ninhydrin (Kaiser, E. et al., *Anal. Biochem.*, 34, 595 (1970)).
   e) Repeating the steps above for the residue γ-Glutamic acid (γ-Glu) which is incorporated as a Boc-derivative or benzyl protected (Boc-Glu-OBzl).
   f) Acidolysis with anhydrous HF to unprotect the tripeptide and release it from the resin.
   g) Purification and characterization of the final products.

Once the tripeptide is formed there is proceeded, as a final step, to the nitrosation of the mercapto group released from its protecting group.

The tests performed demonstrate that the novel S-nitrosated compounds of the invention have a vasodilating the treatment of dysfunctions of the circulatory system, specially at cardiovascular and coronary level.

Consequently, the compounds of the general formula (I), as well as the pharmaceutically acceptable salts of these, may be used, via the use of conventional pharmaceutical techniques, for the preparation of medicaments which may be administered in different manners.

As an example they may be administrated orally in the form of pharmaceutical preparations such as tablets capsules, syrups and suspensions. Parenterally in forms such as in solutions or emulsions, etc. They may also be administrated topically in form of creams, pomades, balsams, etc., and transdermically for example through the use of patches or bandages. They may also be applied directly in the rectum as suppositories. The preparations may comprise physiologically acceptable carriers, excipients, activators, chelating agents, stabilisators, etc. In case of injections there may be incorporated as physiologically acceptable buffers, solubilizing agents or isotonics. The daily dose may be varied depending on the specific symptoms, the age, the body weight of the patients, the specific mode of administration, etc., and a daily normal dose for an adult person could be between 0,1 to 500 mg, and could be administrated as one dose only or divided into several doses during the day.

In the working examples herein (vide infra) are described in details suitable processes to obtain various of the compounds according to the general formula (I). In view of these examples, it is within the skilled persons general knowledge to obtain the compounds not explicitly exemplified herein, via suitable modifications the of working examples herein.

Consequently, the working examples herein should not be interpreted as limiting the scope of the invention, but solely as an additional detailed explication, which guides the skilled person to a more deeply understanding of the invention.

EXAMPLES

In the experimental part of the examples following abbreviations are used:

| AcOEt | ethyl acetate |
|---|---|
| AcOH | acetic acid |
| Boc | terc-butoxycarbonyl |
| Bzl | benzyl |
| DCC | dicyclohexylcarbodiimide |
| DCM | dichloromethane |
| DIEA | N-ethyldiisopropylamine |
| DIP-CI | direct introduction probe - chemical ionization |
| DMF | dimethylformamide |
| DMSO-$d_6$ | dimethylsulfoxide hexa-deuterium |
| EDTA $Na_2$ | ethylendiaminotetraacetic acid sodium salt |
| EtOH | ethanol |
| EtOEt | diethyl ether |
| FAB | fast atomic bombardment |
| COMP | cyclic Guanosine 3',5' monophosphate |
| HPLC | high pressure liquid chromatography |
| MeCN | acetonitrile |
| MeOH | methanol |
| MS | mass spectrometry |
| ODQ | [1H-[1,2,4]oxadizol [4-3a]quinoxalin-1-ona] |
| PyAOP | hexafluorophosphate of 7-azabenzotriazol-1-il-oxitris (pyrrolidine) phosphonium |
| tBuOH | terc-butanol |
| TEA | trifluoroacetic acid |

The chlorhydrates of the start amino acids are synthesized as described in the German patent applications DE-A-3023830 and DE-A-2801849.

The Nuclear Magnetic Resonance spectra have been realized in a Varian Gemini-200 apparatus.

In the $^1$H-NMR spectra are indicated the working frequency and the solvent used to make the spectrum. The position of the signals is indicated in δ (ppm), using as reference the signal of the protons of the solvent. The reference values are 7.24 ppm for the chloroform and 2.49 ppm for the deuterium dimethylsulfoxide. Within brackets are indicated the number of protons corresponding to each signal measured by electronically integration and the type of signal is indicated using following abbreviating: s (single), d (doublet), t (triplet), dd (doublet of doublets), sb (signal broad), sc (signal complex), d.e. $D_2O$ (disappears during realization of the spectrum after addition of some drops of deuterium water.)

In the $^{13}$C-MNR spectra are indicated the working frequency and the solvent on each spectrum. The position of the signals is indicated in δ (ppm), using as reference the signal of the protons of the solvent. The reference values are 77.00 ppm for the chloroform and 39.50 ppm for the deuterium dimethylsulfoxide.

Further, there have been realized magnetic nuclear resonance experiments using the Attached Proton Test (APT).

Analysis by HPLC, to determine the purity of samples, are done under following conditions:

A-General gradient

Column: RP-C18, Symmetry 150×3.9 mm, 5µ, 100 A

Mobile phase: $H_2O+H_3PO_4$ 0.1%/$CH_3CN$+5% $H_2O$+0.1% $H_3PO_4$

Temperature: room temperature

Flow 1 mL/min

Volume of injection: 10 µL ps B-Isocratic

Column: RP-C18, Symmetry 150×3.9 mm, 5µ, 100 A

Mobile phase: 50% de $H_2O+H_3PO_4$ 0.1% y 50% de $CH_3CN$+5% $H_2O$+0.1% $H_3PO_4$ Temperature: room temperature Flow 1 mL/min Volume of injection: 10 µL In the preparation of the tripeptides techniques of preparative chromatography and HPLC are used to purify the crude and the identity of the product is confirmed by mass spectrometry and amino acid analysis. The purity of the tripeptides is analyzed by HPLC under the following conditions: column of type C18 Nucleosyl, 250×4 mm, 120 Å, 10 µm; flow de 1 mL/min; eluents A=$H_2O$ (+0.045% TFA) y B=$CH_3CN$ (+0.036% TFA).

The ultraviolet spectra (UV) have been made by use of a Shimadzu UV-160A spectrophotometer. For each of the compounds is indicated the wave length (λ) in nm and the molecular absorption (ε) in $cm^{-1}$ $mol^{-1}L$.

For high pressure liquid chromatography (HPLC) an ultraviolet photodiode Hewlett-Packard 1040 A detector has been used.

Example 1.

Obtaining N-acetyl-2-amino-2-[4-(4-S-Nitrosomercaptotetrahydropyran)] Acetic Acid (1).

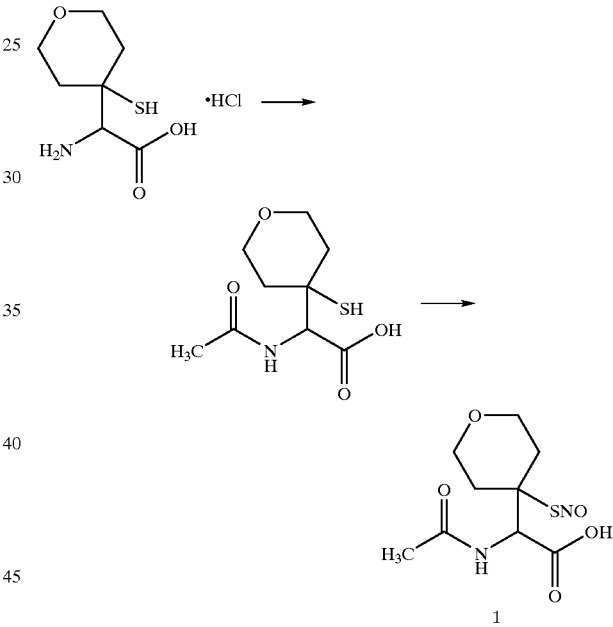

Step 1) In a 250 mL glass flask provided with magnetic agitation 4.0 g. (17.6 mmol) of the chlorhydrate of the 2-amino-2-[4-(4-mercaptotetrahydropyran)] acetic acid and 60 mL of a solution of potassium hydroxide 0.5N are introduced. Afterwards 3.07 g. (21.8 mmol) of anhydrous potassium carbonate and 60 mL of MeCN are added. The mixture is cooled down in an ice bath and 1.42 mL (19.7 mmol) of acetyl chlorine dissolved in 25 mL of MeCN are drop by drop added. Finalized this potassium hydroxide 0.5N is added until pH 9–10. The mixture is agitated at room temperature for 2 hours. Afterwards 2N hydrochloric acid is added until pH=6 and the solvent is eliminated at reduced pressure. The obtained solid is vacuum dried over phosphorous pentoxide, and it is suspended in 150 mL of absolute EtOH and agitated at room temperature. The insoluble residue is filtered and washed with absolute EtOH. The solvent is eliminated at reduced pressure. 3.98 g crude of the intermediate product N-acetyl-2-amino-2-[4-(4-mercaptotetrahydropyran)] acetic acid are obtained, which is submitted to various reverse preparative chromatography phases to obtain 80 mg of the product of 90% of purity (HPLC gradient A, λ=205 nm).

$^1$H-NMR (200 Mhz, DMSO-$d_6$): 7.40 (1H, d, J=10 Hz, NH), 4.13 (1H, d, J=10 Hz, CH), 3.75–3.50 (4H, s.c., $CH_2$), 1.90–1.80 (4H, s.c., $CH_2$), 1.65 (3H, s, $CH_3$)

$^{13}$C-NMR (50 Mhz, DMSO-$d_6$): 171.50 (CO—N), 168.90 (CO), 63.69 ($CH_2$), 63.27 ($CH_2$), 62.80 (CH), 49.18 (C), 37.58 ($CH_2$), 36.12 ($CH_2$), 23.01 ($CH_3$).

Step 2) 80 mg (0.34 mmol) of N-acetyl-2-amino-2-(4-(4-mercaptotetrahydropyran)) acetic acid are dissolved in 4000 μL of MeOH, and afterwards 500 μL of HCl 1 N solution and 136 μL of $NaNO_2$ 5 M solution are added. The resulting solution is treated for 1 minute in an ultrasound bath and afterwards 50 μL NaOH 10 N and 14 μL $H_2O$ are added.

From the resulting solution an aliquot part A of 470 μL is separated and to the rest water in abundance is added, frozen down and lyophilized to obtain 190 mg of a hygroscopic solid B which is slightly humid.

HPLC(gradient A):

λ220 nm: purity of fraction A 68%

λ339 nm: purity of fraction A 95%.

NMR fraction B:

$^1$H-NMR (200 Mhz, DMSO-$d_6$) 8.00–7.50 (1H, s.c., NH), 4.50–4.00 (1H, s.c., CH), 3.80–3.40 (4H, s.c., $CH_2$), 2.40–1.80 (4H, s.c., $CH_2$), 1.88 (3H, s, $CH_3$).

$^{13}$C-NMR (50 Mhz, DMSO-$d_6$): 173.00 (CO), 169.52 (CO), 67.69 ($CH_2$-O), 63.45 (CH), 53.78 (C), 32.17 ($CH_2$), 22.80 ($CH_3$).

Example 2.

Obtaining N-acetyl-2-amino-2-[4-(4-S-nitro-somercapto-1-methylpiperidin)] Acetic Acid (2).

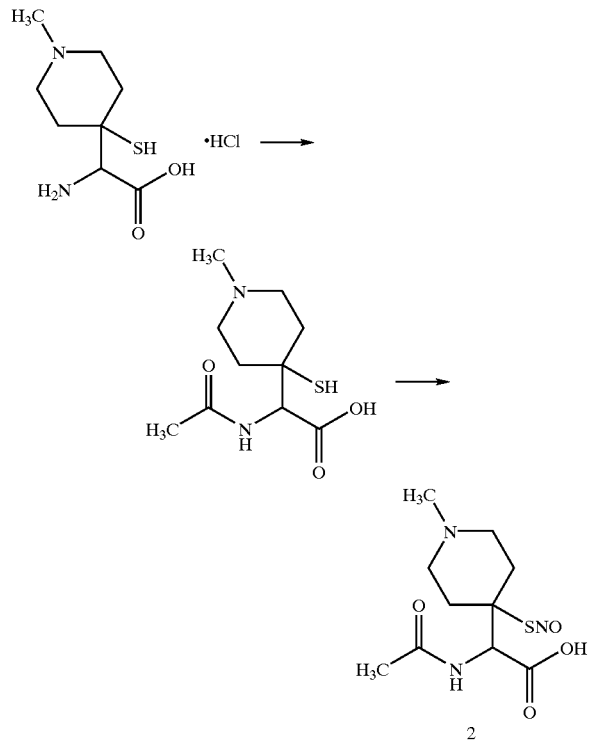

Step 1) In a 250 mL glass flask provided with magnetic agitation 3.69 g (13 mmol) of 2-amino-2-[4-(4-mercapto-1-methylpiperidin)] acetic acid dichlorhydrate and 30 mL of a 0.5N solution of potassium hydroxide are introduced. Afterwards 2.2 g. (16 mmol) of anhydride potassium carbonate and 30 mL of MeCN are added. The mixture is cooled down in an ice bath and 1.0 mL (14 mmol) of acetyl chlorine dissolved in 10 mL of MeCN are drop by drop added. Finalized this, 0.5N potassium hydroxide is added until pH 9–10. The mixture is agitated at room temperature for 2 hours. Afterwards 2N hydrochloric acid is added until pH=6 and the solvent is eliminated at reduced pressure. The obtained solid is vacuum dried over phosphorous pentoxide and the dried solid is suspended in 100 mL of absolute EtOH and agitated at room temperature. The insoluble residue is filtered and washed with absolute EtOH and the solvent is eliminated at reduced pressure. 2.8 g crude of the intermediate product, N-acetyl-2-amino-2-[4-(4-mercaptomethylpiperidin)] acetic acid are obtained, which are submitted to various reverse preparative chromatography phases to obtain 0.5 g of the product of 99% of purity (HPLC gradient A, λ=210 nm).

$^1$H-NMR (200 Mhz, DMSO-$d_6$): 8.35 (1H, d, J=10 Hz, NH), 4.43 (1H, d, J=10 Hz, CH), 3.35–3.00 (4H, s.c., $CH_2$), 2.70 (3H, s, $CH_3$), 2.20–1.90 (4H, s.c., $CH_2$), 1.85 (3H, s, $CH_3$).

$^{13}$C-NMR (50 Mhz, DMSO-$d_6$): 170.55 (CO-N), 170.05 (CO), 61.77 (CH), 49.33 ($CH_2$), 49.28 ($CH_2$), 46.38 (C) 42.26 ($CH_3$), 33.05 ($CH_2$), 33.14 ($CH_2$), 22.42 ($CH_3$).

Step 2) 50 mg (0.20 mmol) of N-acetyl-2-amino-2-[(4-(4-mercapto-1-methylpiperidin)] acetic acid are dissolved in 800 μL of 1 N HCl and afterwards 80 μL of 5 M $NaNO_2$ solution are added. The resulting solution is treated for 1 minute in an ultrasound bath and afterwards 80 μL of 10 N NaOH and 40 μL $H_2O$ are added.

From the resulting solution 100 μL of an aliquot part A are separated and the rest is frozen down and lyophilized to obtain 190 mg of a solid B.

HPLC(gradient A):

λ230 nm: purity fraction A 90%; purity fraction B 93%

λ334 nm: purity fraction A 98%; purity fraction B 98%

NMR Fraction B:

$^1$H-NMR (200 Mhz, $D_2O$): 4.71 (1H, s, CH), 2.70–2.20 (8H, sc, $CH_2$), 1.95 (3H, s., $CH_3$-N), 1.71 (3H, s, $CH_3$—CO).

$^{13}$C-NMR (50 Mhz, $D_2O$): 172.51 (CO), 171.52 (CO), 61.08 (CH), 58.18 (C), 48.09 ($CH_2$—N), 48.01 ($CH_2$—N), 42.18 ($CH_3$—N), 30.44 ($CH_2$), 29.85 ($CH_2$), 20.17 ($CH_3$—CO).

Example 3.

Obtaining N-acetyl-2-amino-3-benzyl-3-S-nitrosomercapto-4-phenyl-butanoic Acid (3).

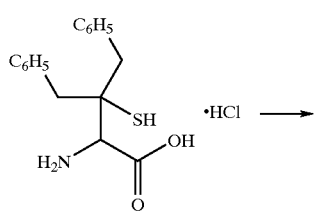

-continued

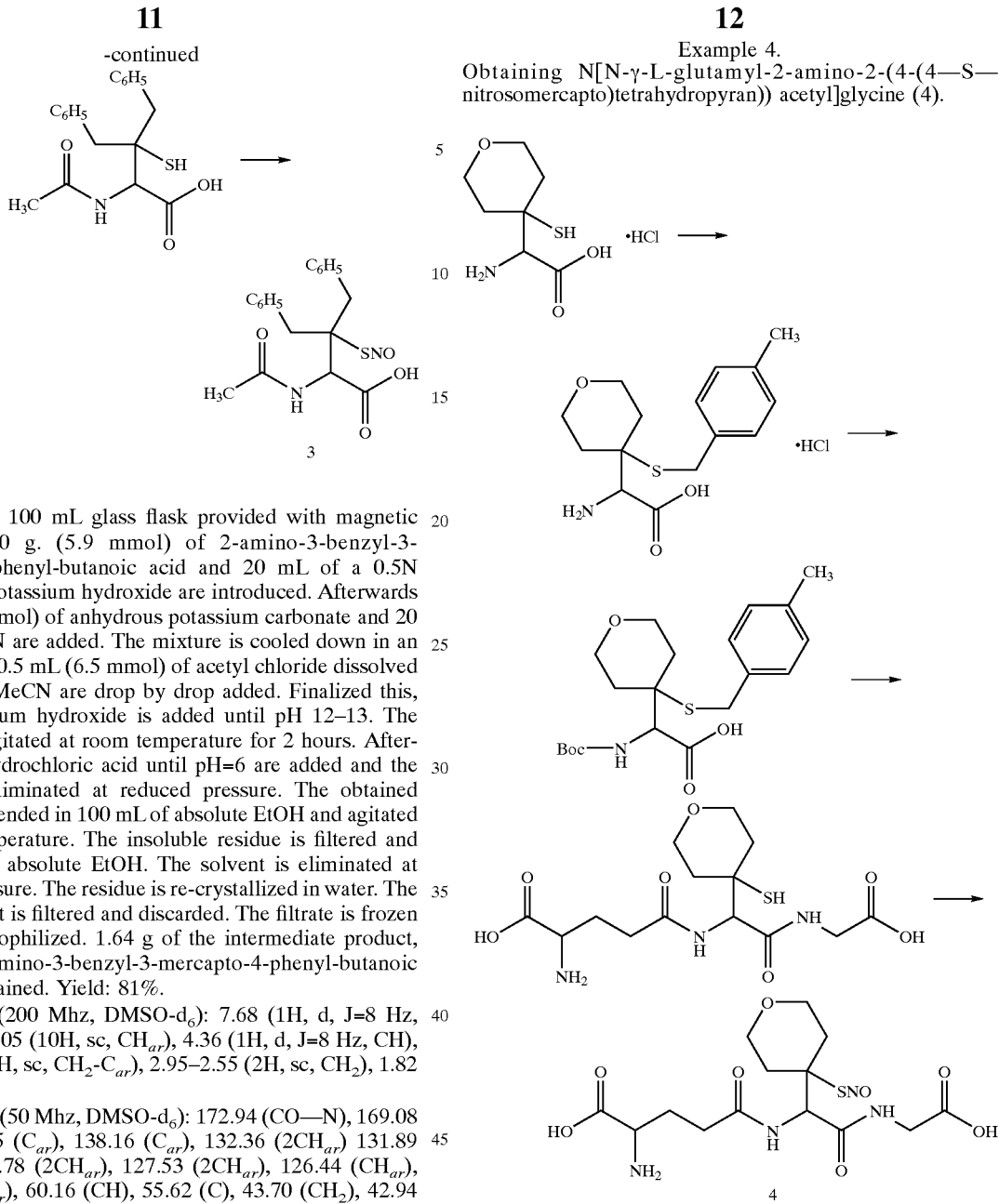

Step 1) In a 100 mL glass flask provided with magnetic agitation 2.0 g. (5.9 mmol) of 2-amino-3-benzyl-3-mercapto-4-phenyl-butanoic acid and 20 mL of a 0.5N solution of potassium hydroxide are introduced. Afterwards 1.0 g. (7.2 mmol) of anhydrous potassium carbonate and 20 mL of MeCN are added. The mixture is cooled down in an ice bath and 0.5 mL (6.5 mmol) of acetyl chloride dissolved in 8 mL of MeCN are drop by drop added. Finalized this, 0.5N potassium hydroxide is added until pH 12–13. The mixture is agitated at room temperature for 2 hours. Afterwards 2N hydrochloric acid until pH=6 are added and the solvent is eliminated at reduced pressure. The obtained crude is suspended in 100 mL of absolute EtOH and agitated at room temperature. The insoluble residue is filtered and washed with absolute EtOH. The solvent is eliminated at reduced pressure. The residue is re-crystallized in water. The insoluble part is filtered and discarded. The filtrate is frozen down and lyophilized. 1.64 g of the intermediate product, N-acetyl-2-amino-3-benzyl-3-mercapto-4-phenyl-butanoic acid, are obtained. Yield: 81%.

$^1$H-NMR (200 Mhz, DMSO-$d_6$): 7.68 (1H, d, J=8 Hz, NH), 7.35–7.05 (10H, sc, CH$_{ar}$), 4.36 (1H, d, J=8 Hz, CH), 3.42–3.02 (2H, sc, CH$_2$-C$_{ar}$), 2.95–2.55 (2H, sc, CH$_2$), 1.82 (3H, s, CH$_3$)

$^{13}$C-NMR (50 Mhz, DMSO-$d_6$): 172.94 (CO—N), 169.08 (CO), 138.55 (C$_{ar}$), 138.16 (C$_{ar}$), 132.36 (2CH$_{ar}$) 131.89 (2CH$_{ar}$) 127.78 (2CH$_{ar}$), 127.53 (2CH$_{ar}$), 126.44 (CH$_{ar}$), 126.26 (CH$_{ar}$), 60.16 (CH), 55.62 (C), 43.70 (CH$_2$), 42.94 (CH$_2$), 23.14 (CH$_3$).

Step 2) 0.62 g (1.8 mmol) of N-acetyl-2-amino-3-benzyl-3-mercapto-4-phenyl-butanoic acid are dissolved in 25 mL of MeOH, and afterwards 25 mL of 1N HCl and 250 mg of NaNO$_2$ solution in 25 mL of H$_2$O are added. The resulting solution is agitated for 35 minutes at room temperature, filtered and washed with water. After drying at reduced pressure in presence of P$_2$O$_5$, 0.33 g of a solid are obtained. HPLC(isocratic B):

λ220 nm: pureza 91%

λ342 nm: pureza 100%

$^1$H-NMR (200 Mhz, DMSO-$d_6$): 8.77 (1H, d, J=10 Hz, NH), 7.28–7.00 (10H, sc, CH$_{ar}$), 5.33 (1H, d, J=10 Hz, CH), 4.12–3.90 (2H, sc, CH$_2$), 3.88–3.38 (2H, sc, CH$_2$), 1.86 (3H, s, CH$_3$)

$^{13}$C-NMR (50 Mhz, DMSO-$d_6$): 171.55 (CO—N), 169.67 (CO—O), 135.51 (C$_{ar}$), 135.27 (C$_{ar}$), 131.52 (CH$_{ar}$), 131.41 (CH$_{ar}$), 128.15 (CH$_{ar}$), 128.05 (CH$_{ar}$), 127.04 (CH$_{ar}$), 65.13 (CH), 56.11 (CH), 40.91 (CH$_2$), 40.15 (CH$_2$), 22.29 (CH$_3$).

Example 4.
Obtaining N[N-γ-L-glutamyl-2-amino-2-(4-(4—S—nitrosomercapto)tetrahydropyran)) acetyl]glycine (4).

Step 1) In a 250 mL glass flask provided with magnetic agitation 5.8 g (25.5 mmol) of of 2-amino-2-(4-(4-mercaptotetrahydropyran)) acetic acid chlorhydrate, 4.7 g (25.5 mmol) of α-bromo-p-xylene, and 100 mL of a mixture of H$_2$O/EtOH 3:1 are mixed. 11 mL of triethylamine are added, an argon atmosphere is made, and the mixture is agitated for 18 hours at room temperature. 50 mL more of H$_2$O/EtOH 3:1 are added and the mixture is agitated for 2 more hours. The resultant suspension is filtered and washed with 100 mL of water and 50 mL of EtOH. A solid is obtained which is dried at reduced pressure. 300 mL of concentrated hydrochloric acid is added over the solid and the solvent is eliminated at reduced pressure. This acid treatment is repeated a second time to obtain a solid which is dried at reduced pressure. 1.59 g of the intermediate product of interest are obtained.

$^1$H-NMR (200 Mhz, DMSO-$d_6$): 8.80–8.30 (3H, sb, H$_3$N+), 7.26 (2H, d, J=8 Hz, CH$_{ar}$), 7.12 (2H, d, J=8 Hz, CH$_{ar}$), 4.03 (1H, s, CH—N), 3.85–3.55 (6H, sc, CH$_2$-C$_{ar}$ CH$_2$—O), 2.26 (3H, s, CH$_3$), 2.05–1.08 (4H, sc, CH$_2$)

$^{13}$C-NMR (50 Mhz, DMSO-d$_6$): 168.98 (CO), 136.64 (C$_{ar}$), 133.80 (C$_{ar}$), 129.55 (CH$_{ar}$) 129.29 (CH$_{ar}$), 62.36 (CH$_2$—O) 59.85 (CH—N), 49.15 (C) 32.03 (CH$_2$), 31.19 (CH$_2$) 30.84 (CH$_2$), 20.69 (CH$_3$).

Step 2) 1004 mg of the chlorhydrate of 2-amino-2-(4-(4-(p-methylbenzylmercapto) tetrahydropyran))acetic acid (3.029 mmol) are suspended in 20 ml of tBuOH/H$_2$O 2:1 and 5% NaOH is added until pH=9. Afterwards 3 equivalents of Boc$_2$O are added and the mixture is left reacting for 30 min, where after the pH is adjusted to pH=9 once more. The reaction is prolonged for 30 min more and the pH is corrected again. comparing with the starting amino acid. By comparing whit the starting amino acid, using thin layer cromatography (TLC), it is confirmed that the reaction has been completed.

The product is isolated by two consecutive extractions with 50 mL of hexane, and the aqueous phase is treated with 1N HCl 1N pH=2. Afterwards three extraction steps with 60 mL of AcOEt in each are made. The solution of AcOEt is dried with anhydrous MgSO$_4$ and, after elimination of the solvent by evaporation, the product is redissolved in DCM and evaporated again. This step is repeated two times more and there to obtain 1191 mg (3.015 mmol) of the N-Boc protected intermediate product.

The product is characterized by:
a) TLC, with CHCl$_3$/MeOH/AcOH 85:10:5 as mobile phase. El Rf=0.48, not observing signal of the starting material.
b) HPLC in gradient from 10% to 100% of MeCN in 30 min+isocratic at 100% of MeCN for 5 min. The resulting purity is of 96% (220 nm)
c) Mass spectrometry by FAB technique: Mcalculated=395, (M+H$^+$) experimental=396.0
d) NMR (CDCl$_3$): 7.18 (2H, d, J=8 Hz) 7.09 (2H, d, J=8 Hz), 5.54 (1H, d, J=11.2 Hz), 4.44 (1H, d, J=8.3 Hz), 3.69 (1H, d, J=11.2 Hz), 3.57 (1H, d, J=11.2 Hz), 3.75–3.98 (4H, sb), 2.32 (3H, s), 1.26–2.19 (4H, sb), 1.46 (9H, s).

Step 3) The tripeptide is prepared by techniques of solid phase synthesis, starting from 1595 mg of a Boc-Gly-OCH$_2$-Pam-resin (Neosystem, ref. No RP00801) of 0.63 mmol/g substitution. The scale of working is of 1.005 mmol.

The general protocol for the addition of the remainder amino is following:
1) Swelling up the resin with 5 washes of 0.5 min with DCM.
2) Removing the Boc group with 40% TFA in DCM, 1×1 min+1×20 min.
3) Washing with DCM, 5×0.5 min.
4) Testing via ninhydrin.
5) Washing with DMF, ×1 min.
6) Coupling for a time period of 1.5 hours.
7) Washing with DMF, 3×1 min.
8) Washing with DCM, 5×0.5 min.
9) Testing via ninhydrin.

In case the test via ninhydrin in the final step iss positive, there is proceeded to re-coupling repeating the steps of 5–8.

The coupling is realized with 6 equivalents (eq) of DIEA, 3 eq. of Boc-amino acid and 3 eq. of active agent, which in this case is PyAOp (hexafluorophosphate of 7-azabenzotriazol-1-il-oxitris (pirrolidino) phosphonium). For the coupling of de γ-Glu is used Boc-Glu-(α-OBzl).

Finalizing the coupling sequence, the resulting peptidyl-resing is submitted to acidolysis with HF/p-cresol (9:1) for 1 hour at 0° C. After evaporation, the solid residue is extracted with anhydrous EtOEt and afterwards the peptide is isolated by extraction with AcOH 10%. Once the volume is reduced by evaporation, the crude is lyophilized and characterized by:
a) HPLC in a gradient from 5% to 65% of MeCN in 30 min.
b) MS by technique of Electrospray:M$_{calc}$=377, (M+H$^+$)$_{exp}$=378.2

The amount of peptide is quantified by amino acid analysis: m=329 mg (0.873 mmol). In all the peptide quantifications the peptide analysis of adding an extern patron of Ile (Isoleucine) to the sample to hydrolyze is used.

The purification of the tripeptide (in two batches) is made through HPLC at preparative scale. The system used is following:
Column: C18 Nucleosyl, 200×20 mm, 120 Å, 10 μm.
Eluents: A=H$_2$O (+0.1% TFA), B=MeCN (+0.1% TFA).
Gradient: Isocratic 0% B for 40 min+gradient de 0% a 10% B en 40 min.
Flow: 25 ml/min.

A total quantity of 227 mg (0.602 mmol) of the intermediate tripeptide is obtained, which is characterized by:
a) HPLC in a gradient from 5% to 45% of MeCN in 20 min. The resulting purity is 95% (220 nm). The minor peak at 8.4 min decreases in relative proportions, until it disappears, by progressively diluting the applied sample. Accordingly, it is concluded that it corresponds to an aggregation of the tripeptide (and not an oxidation) and it is therefore considered as a valid product.
b) MS Electrospray: M$_{calc}$=377 (M+H$^+$)$_{exp}$=378.2

Step 4) To a solution of 14.2 mg (0.38 mmol) of the tripeptide obtained in step 3 in 800 μL of 1N HCl 76 μL of a 0.5M NaNO$_2$ solution are added. Agitation is performed in a ultrasonic bath at room temperature for 1 minute, and afterwards 80 μL of NaOH 10N solution are added. The obtained solution is frozen down and lyophilized and the obtained solid is characterized by:

$^1$H-NMR (200 Mhz, DMSO-d$_6$): 8.90–8.50 (2H, sb, NH), 5.35 (1H, d, J=10 Hz, CH), 4.10–3.00 (3H, sc, CH$_2$, CH), 1.95–1.65 (4H, sc, 2CH$_2$).

$^{13}$C-NMR (50 Mhz , DMSO-d$_6$): 172.18 (CO—N), 171.21 (CO—N), 168.40 (CO—O), 63.03 (CH$_2$), 62.31 (C), 59.56 (CH), 53.19 (CH), 41.20 (CH$_2$), 32.94 (CH$_2$), 31.71 (CH$_2$) 31.41(CH$_2$), 27.12 (CH$_2$)

HPLC (Method A): λ220 nm (purity 94%); λ334 nm (purity 95%)

UV: λ346 nm ε(H$_2$O) 502 cm$^{-1}$ mol$^{-1}$ L

Example 5.

Obtaining N[N-γ-L-glutamyl-2-amino-2-(4-(4-S-nitrosomercapto-1-methyl-piperidin))acetyl ] glycine (5).

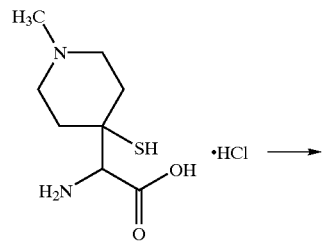

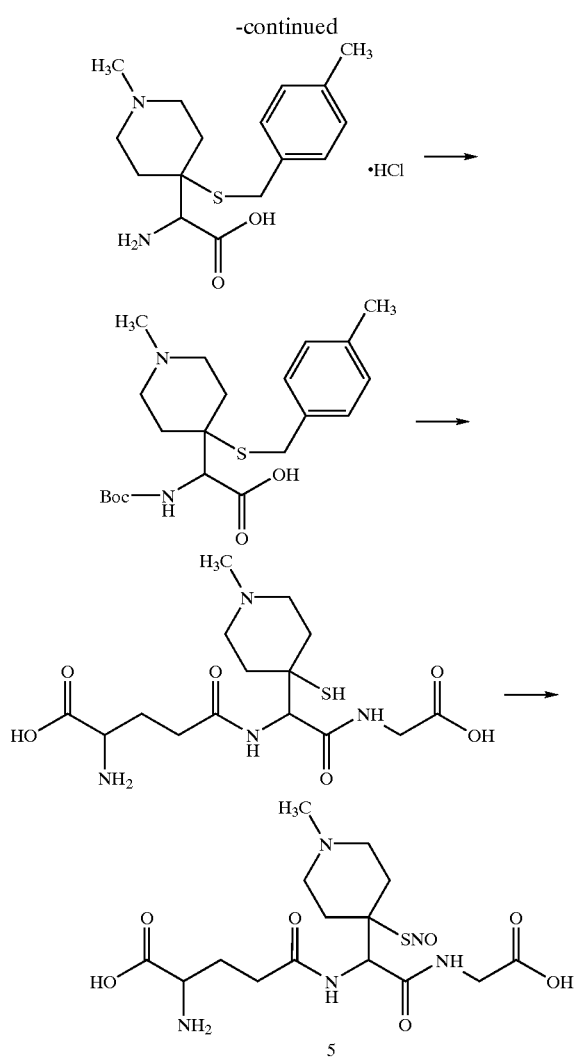

Step 1) In a 100 mL glass flask provided with magnetic agitation 6.4 g (23 mmol) of the dichlorhydrate of 2-amino-2-(4-(4-mercapto-1-methylpiperidin)) acetic acid, 4.3 g (23 mmol) of α-bromo-p-xyleno, and 40 mL of a mixture of $H_2O/EtOH$ 1:1 are mixed. 13 mL of triethylamine are added, an argon atmosphere is created, and the mixture is agitated for 42 h at room temperature. From the resulting solution the solvent is eliminated at reduced pressure and to the obtained crude 20 mL absolute EtOH are added. The obtained solid is filtered and washed successively with absolute EtOH and EtOEt, and it is dried at reduced pressure. 2.11 g of the intermediate product, chlorhydrate of 2-amino-2-(4-(4-(p-methylbenzylmercapto)-1-methylpiperidin))acetic acid, are obtained. Yield: 29.6.

The NMR spectrum are registered in D20 and as reference is taken 4.75 ppm for HDO.

$^1$H-NMR (200 Mhz, $D_2O$): 7.28 (2H, d, J=8 Hz, $CH_{ar}$) 7.15 (2H, d, J=8 Hz, $Ch_{ar}$), 3.64–3.74 (2H, sc, $CH_2$-$C_{ar}$), 3.62 (1H, s, CH—N), 3.4–3.1 (4H, sc, $CH_2$—N), 2.76 (3H, s, $CH_3$—N), 2.24 (3H, s, $CH_3$), 2.15–1.92 (4H, sc, $CH_2$).

$^{13}$C-NMR (50 Mhz, $D_2O$): 173.15 (CO), 141.00 ($C_{ar}$), 136.39 ($C_{ar}$), 132.58 ($CH_{ar}$), 131.95 ($CH_{ar}$), 63.57 (CH—N), 52.48 ($CH_2$)+, 50.65(C), 45.66 ($CH_3$—N), 34.05 ($CH_2$), 32.35 ($CH_2$), 31.28 ($CH_2$), 22.77 ($CH_3$).

Step 2) Starting from 1016 mg (2.958 mmol) of the intermediate obtained in the former step and proceeding in the manner as described in step 2 of example 4, 1016 mg (2.490 mmol) of the N-Boc protected intermediate are obtained, which is characterized by:

a) CCF (mobile phase $CHCl_3$/MeOH/AcOH 85:10:5). $R_f$=0.32, without the signal of the starting product is observed.

b) HPLC gradient from 10% to 100% of MeCN in 30 min. The purity is 96% (220 nm).

c) MS by FAB technique: $M_{calc}$=408 $(M+H^+)^{exp}$=408.9 d) MS by Electrospray technique: $(M+H^+)_{exp}$=409.3

Step 3) The tripeptide intermediate is obtained, using the method described in step 3 of example 4, starting from 794 mg of the resin mentioned above. The working scale is 0.5 mmol. Due to the difficulties of solubilizing the Boc-derivative it is chosen to use N-methylmorpholine as base (3 equivalents) in stead of DIEA in the coupling reaction mentioned above. After the incorporation of γGlu, the tripeptide is assembled and the peptide-resin bond is broken by acidolysis in the same way as described above. Finally a crude in 10% AcOH is obtained which is lyophilized and quantified afterwards. 137 mg (0.351 mmol) of the intermediate tripeptide are obtained and characterized by:

a) HPLC, isocratic gradient 0% for 10 min+5%→65% of MeCN for 30 min. It is seen that the injected product in acetic solution elutes with the front, which makes it necessary to lyophilize the aliquots to eliminate the acid and re-dissolve the lyophilizate in 1mM HCl. In this way the peptide could be observed chromatographic and it elutes at 6.8 min in the gradient used.

b) MS by Electrospray technique: Mcalc=390 $(M+H^+)_{exp}$=391.2

The purification of the crude is performed via HPLC, at preparative scale, with the parameters already described in example 4. There is also applied an isocratic of 0% of B for 40 min followed by a gradient from 0% to 10% of B for 40 min. In this way 107 mg (0.274 mmol) of the product are obtained, characterized by:

a) HPLC gradient from 0% to 0% for 10 min plus 0% to 30% for 20 min. The purity is 94% (220 nm). It is confirmed that the additional peak at 8.0 min corresponds in this case too to aggregation and this is accordingly assigned to correct product.

b) MS by Electrospray technique: Mcalc=390 $(M+H^+)_{exp}$ 391.1

Step 4) Starting from 10.0 mg (0.026 mmol) of the tripeptide intermediate obtained in the former step the nitrosation is performed as described in step 4 of example 4, using 52 μL of 0.5M $NaNO_2$. The obtained product is characterized by:

$^{13}$C-NMR (50 Mhz, DMSO-$d_6$): 171.57 (CO—N), 170.99 (CO—N), 170.76 (CO—N), 168.20 (CO—O), 60.23 (C), 59.53 (CH), 51.57 (CH), 49.02 ($CH_2$), 42.20 ($CH_3$), 41.59 ($CH_2$) 30.49 ($CH_2$), 29.75($CH_2$), 29.31 ($CH_2$), 26.05 ($CH_2$)

HPLC (Method B): λ220 nm (purity 74%); λ334 nm (purity 88%).

UV: λ346 nm ε($H_2O$) 198 $cm^{-1}$ $mol^{-1}$ L

Example 6.
Obtaining N[N-γ-L-glutamyl-2-amino-3-benzyl-3-(S-nitrosomercapto)-4-phenylbutanoyl ] glycine (6)

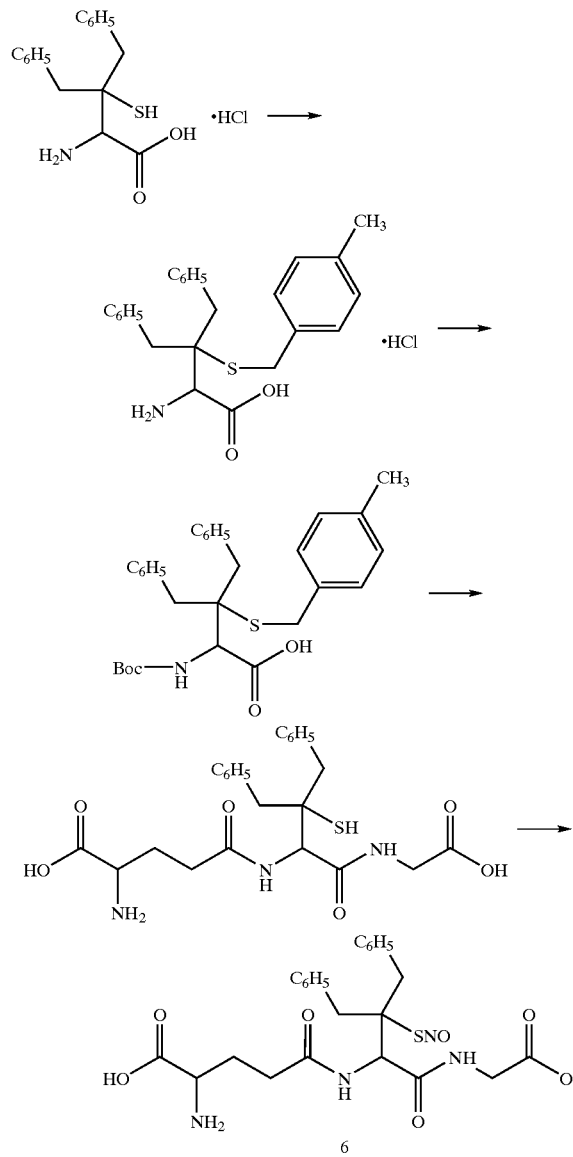

Step 1) In a 100 mL glass flask provided with magnetic agitation 1.25 g (3.7 mmol) of the chlorhydrate of 2-amino-3-benzyl-3-mercapto-4-phenylbutanoic acid, 0.68 g (3.7 mmol) de α-bromo-p-xylene, and 40 mL of a mixture of H$_2$O/EtOH 1:1 are mixed. 1.6 mL of triethylamine are added and the major part of the suspended solid is dissolved. An argon atmosphere is created and the mixture is agitated for 24 h at room temperature. The ethanol and part of the triethylamine are eliminated at reduced pressure. The resulting aqueous suspension is filtered and a white solid is obtained. It is purified via reverse phase column chromatography with CH$_3$CN—H$_2$O. 100 mL of MeOH/HCl 1:1 are added over the obtained solid and the solvent is eliminated at reduced pressure. 0.5 g of the intermediate product, chlorhydrate of 2-amino-3-benzyl-3-(4-methylbenzylmercapto)-4-phenylbutanoic acid, are obtained.

$^1$H-NMR (200 Mhz, DMSO-d$_6$): 8.95–8.50 (3H, sb, H$_3$N+), 7.45–7.25 (10H, SC, CH$_{ar}$), 7.08 (2H, d, J=10 Hz, CH$_{ar}$) 6.98 (2H, d, J=10 Hz, CH$_{ar}$), 4.05 (1H, s, CH—N), 3.55–3.0 (4H, SC, CH$_2$—C$_6$H$_5$, CH$_2$-C$_{ar}$), 2.90–2.60 (2H, SC, CH$_2$) 2.20 (3H, S, CH$_3$)

$^{13}$C-NMR (50 Mhz, DMSO-d$_6$): 168.70 (CO), 136.53 (C$_{ar}$), 136.00 (C$_{ar}$), 134.94 (C$_{ar}$), 132.50 (C$_{ar}$), 131.18 (CH$_{ar}$) 129.169 (CH$_{ar}$), 128.90 (CH$_{ar}$), 128.26 (CH$_{ar}$), 128.02 (CH$_{ar}$) 127.07 (CH$_{ar}$), 57.06 (CH—N), 53.64 (C) 42.22 (CH$_2$), 41.65 (CH$_2$), 31.90 (CH$_2$S), 20.$_{48}$ (CH$_3$).

Step 2) Starting from the two fractions obtained in the former step (180 mg of the 83% of purity and 530 mg of the 94% of purity) and proceeding as described in step 2 of example 4, 733 mg (1.45 mmol) of the intermediate N-Boc protected product are obtained and characterized by:

a) CCF (CHCl$_3$-MeOH-HOAc 85:10:5), Rf=0.63.

b) HPLC Gradient from 10% to 100% MeCN, 30 min, isocratic 100%, 5 min, purity: 91% (220 nm)

c) EM-MALDI-TOF (mass spectrum): Matrix of dihydroxybenzoic acid, M$_{calc}$=505 (M+H$^+$)$_{exp}$=528.585 (M+Na)

d) NMR: The presence of the Boc group is confirmed.

Step 3) The tripeptide intermediate is obtained, using the method described in step 3 of example 4, starting from 0.43 mmol of the resin mentioned above. After the acidolytic step a crude is isolated which contains 14.4 mg (29.96 μmol) of the tripeptide intermediate which is characterized by:

a) HPLC analytic gradient from 5% to 65% for 30 min, approximated purity 95%.

b) EM-electrospray M$_{calc}$=487(M+H$^+$), M$_{exp}$=488.3

Step 4) Starting from 5.7 mg (0.012 mmol) of the tripeptide intermediate obtained in the former step, the nitrosation is effectuated as described in step 4 of example 4, using 24 μL of 0.5 M NaNO$_2$. The product obtained is characterized by:

HPLC (Method A): λ220 nm purity 68%; λ334 nm purity 86%.

UV: λ345 nm ε(H$_2$O) 368 cm$^{-1}$ L.

Example 7.
Tests for In Vitro Vasodilatation.

The method used in the assays is substantially the same as described in the following references:

Furchgot, R. F. "Methods in nitric oxide research". Feelisch & Stamler eds. John Wiley &Sons, Chichester, England, pp 567–581.

Trongvanichnam, K, et al. Jpn J. Pharmacol. 1996; 71:167–173.

Salas, E., et al. Eur. J. Pharmacol. 1994; 258:47–55.

The compounds are tested at 5 different concentrations, at a concentration range from 0,001 y 10 mM, using from 6 to 9 arterial rings for each compound. The obtained results are compared to those from the S-nitrosoglutathione (GSNO), which is used as reference product.

The results are shown in table 1 below and are provided as CE$_{50}$ (concentration effective 50), which is the concentration of each of the tested compounds wherein there is produced a vasodilatation of 50% of the arterial ring previously contracted with 1 μM of Norepinephrine.

TABLE 1

Test of vasodilatation

| Compound | CE$_{50}$ μM (average ± SD) |
|---|---|
| GSNO | 1.56 ± 0.55 |
| Product obtained in example 1 | 0.375 ± 0.05 |

TABLE 1-continued

Test of vasodilatation

| Compound | $CE_{50}$ $\mu M$ (average ± SD) |
|---|---|
| Product obtained in example 2 | 0.024 ± 0.003 |
| Product obtained in example 3 | 0.63 ± 0.21 |
| Product obtained in example 4 | 1.73 ± 0.27 |
| Product obtained in example 5 | 1.89 ± 0.82 |

As it can be observed, all the compounds tested have a potent vasodilating activity, similar or superior to that of the reference compound (GSNO), and the compound 2 has a vasodilating activity highly superior to that of the reference product.

Example 8.
Tests In Vitro of the Inhibition of the Aggregation of the Platelets.

The method used in the assays is substantially the same as described in following references:

Loscalzo J, et al. En: Methods in nitric oxide research (Feelisch M, Stamler JS, eds.) John Wiley & Sons, Chichester, England, pp 583–591.
Radomski MW, et al. Br J Pharmacol 1987;92:181–187.
Salas E, et al. Br J Pharmacol 1994;112:1071–1076.

The compounds are tested at four different concentrations, using platelets from 5 to 23 different donors. The obtained results are compared to those from the S-nitrosoglutathione (GSNO), which is used as reference product.

The results are shown in table 2 and are expressed as $CI_{50}$ (concentration of inhibition 50), which is the concentration of each of the tested compounds wherein there is produced an inhibition of 50% of aggregation obtained with a sub-maximal collagen concentration (1 $\mu g/mL$).

TABLE 2

Tests of inhibition of the aggregation of the platelets.

| Compound | $IC_{50}$ $\mu M$ (average ± SD) |
|---|---|
| GSNO | 0.48 ± 0.19 |
| Product obtained in example 1 | 0.07 ± 0.02 |
| Product obtained in example 2 | 0.19 ± 0.02 |
| Product obtained in example 3 | 0.24 ± 0.027 |
| Product obtained in example 4 | 0.20 ± 0.12 |
| Product obtained in example 5 | 0.047 ± 0.011 |
| Product obtained in example 6 | 0.35 ± 0.11 |

As it can be observed in table 2, all the compounds tested have a potent inhibiting activity on aggregation of the platelets, similar or superior to that of the reference compound (GSNO), and the compounds 1 and 5 have an inhibiting activity on platelets aggregation highly superior to that of the reference product.

Example 9.
Tests In Vitro of the Increase of the Intra-platelet Levels of GMPc.

The compound obtained in example 5 (5) is tested in vitro to test its capacity to increase the intra-platelet levels of GMPC in a preparation of human washed platelets.

The method used in the test is substantially the same as described in the references cited in example 8.

The compounds are tested at four different concentrations, using different platelets from 5 donors. The obtained results are compared to those from the GSNO (reference product) and with the basal values. The results are shown in table 3, expressed as pmol/$10^9$ platelets.

TABLE 3

Test of the increase of the intra-platelet levels of GMPc.

| | GMPc (pmol/$10^9$ platelets) | |
|---|---|---|
| [$\mu M$] | GSNO | Compound 5 |
| 3 | 27.6 ± 6.0 | — |
| 1 | 24 ± 0.5 | 21.1 ± 0.5 |
| 0.3 | 6.6 ± 0.6 | 6.50 ± 0.5 |
| 0.1 | 1 ± 0.5 | 1.50 ± 0.4 |
| 0.03 | — | 1.60 ± 0.5 |
| 0 | 1.33 ± 0.38 | 1.33 ± 0.38 |

The compound 5 increases the intra-platelet levels of GMP in a similar manner to that of the GSNO reference. It should be mentioned that for values close to the $IC_{50}$ the compound 5 induces levels of GMPc lower as that of the GSNO when it is used at concentrations close to its $IC_{50}$.

Example 10.
Test In Vitro of the Blockage of Platelet Aggregation Inhibition.

The method used in the test is substantially the same as described in the references cited in example 8, completed with the reference:

Moro MA, et al. Pr Nat Acad Sc USA. 1996 ;93:1480–5.

The ODQ is tested in vitro to block the inhibition of platelet aggregation reached by the obtained products in human washed platelet preparations.

The compound obtained in example 5 (5) is tested at three different concentrations, in presence and absence of ODQ (1 $\mu M$), using platelets from 5 different donors. The obtained results are compared to those from the GSNO (reference product) and with the values in absence of ODQ. The results are shown in tables 4 and 5 and expressed as the percentage of inhibition of the maximum aggregation.

TABLE 4

| | Reference product (GSNO) | |
|---|---|---|
| [$\mu M$] | % inhibition without ODQ | % inhibition with ODQ |
| 1 | 92.65 ± 0.9 | 32.65 ± 0.9 |
| 0.3 | 79.33 ± 17 | 3.3 ± 3 |
| 0.1 | 34.2 ± 25 | 0 |

TABLE 5

| | Compound 5 | |
|---|---|---|
| [$\mu M$] | % inhibition without ODQ | % inhibition with ODQ |
| 0.3 | 96 | 0 |
| 0.1 | 96 | 0 |
| 0.03 | 83 ± 1.4 | 0 |
| 0.01 | 17 | 0 |
| 0.003 | 0 | 0 |

The ODQ (1 $\mu M$) is capable of blocking the inhibiting effect of GSNO and the compound 5, when the $IC_{50}$ dose of the compounds is used. At higher doses to that of the $IC_{50}$, the effect of inhibition of the aggregation is better blocked in the case of the compound 5 as compared to the case of the reference product.

What is claimed is:

1. An S-nitrosothiol derivative of penicillamine or glutathione of formula I:

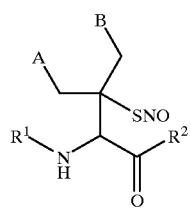

(I)

or its pharmaceutically acceptable salt thereof, in which:
A and B are phenyl groups or together form the group —CH$_2$—Q—CH$_2$— constituting a six membered ring in which Q represents oxygen, sulfur, or a group N—R$^3$, in which R$^3$ is hydrogen or an alkyl group C$_1$–C$_4$;
R$^1$ is an acyl group, which may be an aliphatic C$_1$–C$_5$ acyl group or a glutainic acid acyl group bonded via its gamma carboxyl group;
R$^2$ is a hydroxyl group or a glycine group bonded via a peptide bond; with the proviso that if R$^1$ is an aliphatic acyl group, then R$^2$ is a hydroxyl group, and if R$^1$ is a glutamic acid acyl group, then R$^2$ is a glycine group.

2. The S-nitrosothiol derivative of claim 1 having the formula:

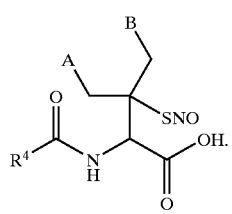

(II)

wherein R$^4$ is a C$_1$–C$_4$ alkyl group.

3. The S-nitrosothiol derivative of claim 1 which is N-acetyl-2-amino-2-[4-(4-S-nitrosomercaptotetrahydropyran)] acetic acid.

4. The S-nitrosothiol derivative of claim 1 which is N-acetyl-2-amino-2-[4-(4-S-nitrosomercapto-1-methylpiperidin)] acetic acid.

5. The S-nitrosothiol derivative of claim 1 which is N-acetyl-2-amino-3-benzyl-3-S-nitrosomercapto-4-phenlylbutanoic acid.

6. The S-nitrosothiol of claim 1, having the following formula III:

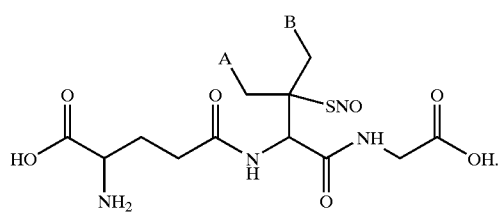

(III)

7. The S-nitrosothiol derivative of claim 1 which is N[N-γ-L-glutamyl-2-amino-2-(4-(4-S-nitrosomercapto) tetrahydropyran))acetyl]glycine.

8. The S-nitrosothiol derivative of claim 1 which is N[N-γ-L-glutamyl-2-amino-2-(4-(4-S-nitrosomercapto-1-methylpiperidin))acetyl]glycine.

9. The S-nitrosothiol derivative of claim 1 which is N[N-γ-L-glutamyl-2-amino-3-benzyl-3-(S-nitrosomercapto)-4-phenylbutanoyl]glycine.

10. A pharmaceutical composition comprising a the S-nitrosothiol derivative of claim 1 and a pharmaceutical carrier therefor.

11. The pharmaceutical composition according to claim 10 wherein the S-nitrosothiol derivative has the formula

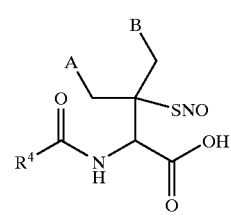

(II)

wherein R$^4$ is a C$_1$–C$_4$ alkyl group.

12. The pharmaceutical composition according to claim 10 which is N-acetyl-2-amino-2-(4-(4-S-nitrosomercaptotetrahydropyran)] acetic acid.

13. The pharmaceutical composition according to claim 10 which is N-acetyl-2-amino-2-[4-(4-S-nitrosomercapto-1-methylpiperidin)] acetic acid.

14. The pharmaceutical composition according to claim 10 which is N-acetyl-2-amino-3-benzyl-3-S-nitrosomercapto-4-phenylbutanoic acid.

15. The pharmaceutical composition according to claim 10 wherein the S-nitrosothiol derivative has the formula

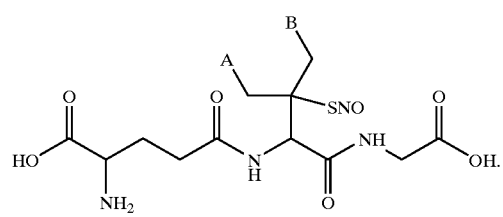

(III)

16. The pharmaceutical composition according to claim 10 wherein the S-nitrosothiol derivative is N[N-γ-L-glutamyl-2-amino-2-(4-(4-S-nitrosomercapto)tetrahydropyran))acetyl]-glycine.

17. The pharmaceutical composition according to claim 10 wherein the S-nitrosothiol derivative is N[N-γ-L-glutamyl-2-amino-2-(4-(4-S-nitrosomercapto-1-methylpiperidin))acetyl]glycine.

18. The pharmaceutical composition according to claim 10 wherein the S-nitrosothiol derivative is N[N-γ-L-glutamyl-2-amino-3-benzyl-3-(S-nitrosomercapto)-4-phenylbutanoyl]glycine.

19. A method of inhibiting vasoconstriction comprising administering the S-nitrosothiol derivative according to claim 1 to a subject in need thereof for a time and under conditions effective to inhibit vasoconstriction.

20. A method of inhibiting platelet aggregation comprising administering the S-nitrosothiol derivative according to claim 1 to a subject in need thereof for a time and under conditions effective to inhibit platelet aggregation.

21. A method of inhibiting platelet aggregation comprising contacting platelets with the the S-nitrosothiol derivative according to claim 1 for a time and under conditions effective to inhibit aggregation of said platelets.

22. A method of stimulating platelets to produce cGMP comprising administering the S-nitrosothiol derivative according to claim 1 to a subject in need thereof for a time and under conditions effective to stimulate said platelets to produce cGMP.

23. A method of stimulating platelets to produce cGMP comprising contacting platelets with the S-nitrosothiol derivative according to claim 1 for a time and under conditions effective to stimulate said platelets to produce cGMP.

* * * * *